United States Patent [19]

Hill et al.

[11] Patent Number: 4,942,034
[45] Date of Patent: Jul. 17, 1990

[54] DENTAL STIMULATOR

[76] Inventors: Ira D. Hill, Clay Court, Locust, N.J. 07760; Robert D. White, 65 Glen Gray Rd., Oakland, N.J. 07436

[21] Appl. No.: 270,165

[22] Filed: Nov. 14, 1988

[51] Int. Cl.$^5$ .................. A61K 7/16; A61K 7/18; A61C 15/00; A46B 9/04
[52] U.S. Cl. .................... 424/401; 132/321; 132/329; 424/49; 424/52; 424/435; 424/443; 433/215; 433/216
[58] Field of Search .................... 132/321–329; 433/215–216; 424/49, 52, 435, 443, 401

[56] References Cited

U.S. PATENT DOCUMENTS

| | | | |
|---|---|---|---|
| 2,667,443 | 4/1954 | Ashton | 132/321 |
| 2,748,781 | 6/1956 | Collat | 424/52 |
| 2,772,205 | 11/1956 | King | 424/443 |
| 2,896,639 | 7/1959 | Fleming | 132/321 |
| 3,838,702 | 10/1974 | Standish et al. | 132/321 |
| 3,897,795 | 8/1975 | Engel | 132/321 |
| 4,029,113 | 6/1977 | Guyton | 132/321 |
| 4,175,326 | 11/1979 | Goodson | 424/435 |
| 4,462,136 | 7/1984 | Nakao et al. | 132/329 |
| 4,510,127 | 4/1985 | Chang | 424/49 |
| 4,627,975 | 12/1986 | Lynch | 424/49 |

FOREIGN PATENT DOCUMENTS 55-90555  7/1980  Japan ............................ 433/216

Primary Examiner—Shep K. Rose
Attorney, Agent, or Firm—Ernest V. Linek

[57] ABSTRACT

The present invention discloses a dental stimulator, e.g., one or more segments of wood (balsa, birch, bass, etc.) treated with one or more surfactants or emulsifiers (as a cleaning substance) and one or more coating substances, insoluble in said cleaning substance. The loading rate for these materials ranges from about 5 mg to about 50 mg per segment of the dental stimulator.

6 Claims, No Drawings

DENTAL STIMULATOR

BACKGROUND OF THE INVENTION

The present invention relates to oral hygiene and specifically to the frequent cleansing of the oral cavity and interference with the formation of plaque. Plaque is a microbial coating on tooth surfaces, bound together by natural polymers, (mucopolysaccharides,) formed by microbial action on the cell debris, food remnants, sugars and starches in the mouth. Embedded in this polymer matrix are the bacteria normal to the oral cavity but, when trapped against tooth surfaces and protected by the matrix from easy removal, are in excellent position for "mischief." Most dental texts implicate plaque in the formation of caries, or tooth decay. In addition, these embedded bacteria release toxins that cause gingivitis, bleeding and swelling of the gums. Gingivitis can lead to periodontitis in which gums recede, pockets of infection form and teeth loosen.

Plaque formation is an ongoing process. Various gel and paste dentifrice preparations, mouth rinse and mouth prerinse preparations make plaque and/or tartar control claims One disadvantage of these preparations is that only a relatively short time during which the teeth are being cleaned or the mouth is being rinsed is available for these preparations to take effect. These preparations generally have little residual effect on plaque formation. Additionally, some of these preparations such as mouth rinses and prerinses contain various antimicrobial substances which may alter the critically balanced microflora of the mouth. Another disadvantage of these preparations is the general infrequency of use. That is, most are used once or perhaps twice daily and seldom when they are most needed, e.g., after meals, snacks, smoking, drinking, coffeebreaks, etc.

Effective oral hygiene requires that three control elements be maintained by the individual:

1. Physical removal of stains, plaque and tartar. This is accomplished in the strongest sense by scraping and abrasion in the dentist's office. Self administered procedures are required frequently between visits and range from tooth brushing with an appropriate abrasive toothpaste through flossing and water jet action down to certain abrasive foods and even the action of the tongue against tooth surfaces.

2. Surfactant Cleansing. This is required to remove: food debris and staining substances before they adhere to the tooth surfaces; normal dead cellular (epithelial) material which is continually sloughed off from the surfaces of the oral cavity and microbial degradation products derived from all of the above. Besides the obvious hygenic and health benefits related to simple cleanliness provided by surfactants, there is an important cosmetic and sense-of-well-being benefit provided by surfactant cleansing. Research has shown that the primary source of bad breath is the retention and subsequent degradation of dead cellular material sloughed off continuously by the normal, healthy mouth.

3. Frequency of Cleansing. This is perhaps the most difficult to provide in today's fast-paced work and social environment. Most people recognize that their teeth should be brushed at least 3 times a day *plus* after each snacking occasion.

The simple fact is that most of the population brush once a day, some brush morning and evening, but precious few carry toothbrush and dentifrice to use the other three or four times a day for optimal oral hygiene. Consumer research suggests that the population brushes an average of 1.3 times a day. Thus, the 24 hour period between brushings for a majority of the population provides optimum plaque forming conditions with no interruptions.

Since plaque is regarded by most of the dental profession as a causitive agent leading to various dental pathologies as noted above, there is considerable desire by most consumers to remove or prevent the formation of plaque on a daily basis. There are three oral care strategies which address the problem of plaque: abrasion, anti-microbial agents and removal of precursors to plaque.

1. Abrasive removal of the plaque film, once it has firmly adhered to the tooth surface, is the only totally effective cleansing mechanism. Again, professional dental hygiene is the most effective, but recently a number of special abrasive toothpastes have been accepted by dental organizations as partially removing adhered plaque and the tartar which subsequently forms from the plaque.

2. Antimicrobial action could affect plaque formation in two ways, (a) reducing the number of bacteria in the mouth which form the mucopolysaccharides and (b) killing those bacteria trapped in the film to prevent further growth and metabolism. However, the medical and dental community is divided about the advisability of frequent use of antimicrobial agents in the mouth in rinses or prerinses, especially the most effective ones, except under strict supervision of licensed practitioners. There are a number of reasons given, but one concern is that such materials would upset the ecological balance of the mouth. A balanced, "friendly" microbial population is necessary to prevent pathogenic organisms from taking over.

3. Removal of plaque precursors requires the reduction of food sources and building blocks required for the bacteria to synthesize the mucopolysaccharides which polymerize into the plaque film. Going far back into the chain of events leading to plaque formation and interrupting the chain has much to commend it as a sound oral hygiene strategy. However, for this strategy to be effective, the plaque building blocks must be interrupted periodically. As noted above, hereto, the oral hygiene preparations described about fall short on "frequency-of-use" basis.

For reference, see, L. Menaker, *The Biologic Basis of Dental Caries*, Chapters 5, 11, 12, 14 16 and 18, Harper & Row (1980).

SUMMARY OF THE INVENTION

It has now been found that plaque formation can be disrupted by periodically stimulating the gums with a dental stimulator treated with the compositions of this invention into the mouth. This interference with the plaque forming process is carried out without substantially altering the critically balanced microflora of the mouth. The compositions of the present invention contain a combination of cleaning and coating substances in a sprayable liquid dentifrice that leaves the mouth with a prolonged clean, just-brushed feeling.

The present invention combines two of the three primary elements of oral hygiene, namely surfactant cleansing and frequent cleansing. The latter element is especially important in that it is the product difference which no previous oral hygiene product has successfully implemented. Plaque fighting of the present invention is based on a unique novel interruption theory conveniently reduced to practice, i.e., the disruption of plaque formation without resort to antimicrobial ingredients. This interruption of plaque formation is further enhanced by the presence of a smooth, thin film of coating substance in the oral cavity which makes it more difficult for plaque to attach to the teeth. The present invention represents the next major advance in oral hygiene after regular brushing with an abrasive dentifrice paste/or rinsing with various plaque fighting rinses and prerinses.

DETAILED DESCRIPTION OF THE PREFERRED EMBODIMENT

The present invention is especially directed to a treated dental stimulator comprising: one or more segments of a wooden dental stimulator suitable for stimulating gums selected from the group of stimulators comprising balsa, birch and bass wood loaded with a surfactant or emulsifier (i.e., cleaning substance) and one or more coating substances insoluble in said cleaning substance, at a rate between about 5 mg and about 50 mg per segment of the stimulator.

The cleaners include: surfactants and emulsifiers sodium lauryl sulfate,
sodium lauroyl sarcosinate,
polyethyleneglycol stearate,
polyethyleneglycol monostearate,
coconut monoglyceride sulfonates,
soap powder,
sodium alkyl sulfates,
sodium alkyl sulfoacetates,
alkyl polyglycol ether carboxylates such as those described in U.S. Pat. No. 4,130,636
polyoxyethylene derivatives or sorbitan esters, such as those described in U.S. Pat. Nos. 3,639,563; 3,947,570,
propoxylated cetyl alcohol as described in U.S. Pat. No. 2,677,700; and
preferred commercially available substances which include:
polyoxyethylene - polyoxybutylene block copolymers such as Pluronic F108, and F127 (BASF) and polysorbates such as Tween 40, and 80, (Hercules).
Particularly preferred surfactants include block copolymers comprising a cogeneric mixture of conjugated polyoxybutylene and polyoxyethylene compounds having as a hydrophobe, a polyoxybutylene polymer of at least 1200 molecular weight; such as described in U.S. Pat. Nos. 4,343,785; 4,465,663; 4,511,563 and 4,476,107, and The coating substances can be characterized in that they:

(1) suppress the tendency of the surfactant cleaners present to foam, (2) are safely ingentible at the concentrations used, (3) have an affinity for mouth and teeth surfaces, (4) are neutral, inert and do not support biological activity, (5) modify the surface energy properties of surfaces of the mouth such that it is more difficult for food particles, cellular debris and various plaque precursors and formers to attach to these surfaces, (6) form a thin, transparent coating that does not build up on mouth surfaces and is removed by the normal clearing and flushing action of the mouth, (7) impart a pleasant "smooth" feeling to the surfaces of the mouth and teeth, and (8) retain various flavors and substances on surfaces of the mouth imparting an unexpected prolonged flavor effect.

(9) the coating substances include various silicones, long chain hydrocarbons, carbowaxes and polymers such as:
silicone glycol co-polymers,
polydimethyl siloxanes,
long chain hydrocarbons, especially normal paraffins having a chain length of 16 carbon atoms or greater, paraffins with several loci of branching and unsaturation, where the extend of such branching and unsaturation does not create unacceptable toxicity nor lower the solidification point below body temperature, Carbowaxes ® (polyethylene glycols), and polymers which have limited solubility in ethanol and water solutions where the ethanol: water ratio is greater than 0.3:1 but have essentially no solubility in water or saliva at lower ratios.

The combination of certain cleaners with certain coating substances, wherein the latter is inherently insoluble in the former, as an additive to a dental stimulator is novel. The results obtained with a stimulator containing this combination in the mouth, is novel. Furthermore, the cleaner/coating substance/saliva mixture obtained in the mouth is ingestible and can be pleasantly swallowed, which further distinguishes it from typical dentrifices used with a toothbrush and most rinses and prerinses. For example, unlike typical cleaners used in dentifrice pastes, the cleaners of the present invention do not fill the mouth with foam and can be pleasantly swallowed which is necessary for the high frequency cleaning feature of the present invention.

Surprisingly, the cleaning/coating combination of the present invention retains good surface active properties and is able to clear the mouth of some cell debris, food debris, material alba, sugars, starches and other precursors to plaque This cleaning is obtained with minimal foaming while simultaneously coating the surfaces of the oral cavity with a thin neutral film containing the flavorants of the composition. This neutral film is not metabolizable by resident oral cavity microorganisms.

By contrast, natural film formers such as lecithin-containing substances and fats are known to form anti-attachment films on mouth surfaces but these films are not suitable for the purposes of the present invention since they are metabolizable and are not neutral. Most of these naturally occurring coating substances support biological activity rather than form non-supportive inert films and as such, work opposite of the suitable film formers of the present invention. See for example; Menaker, *The Biologic Basis of Dental Caries*, Chapter 16; Gibbons and Hoote, *Ann. Rev. of Microbiol*, 29, pp. 19–44; and Hayes, *J. Dent. Res.*, 632, pp. 2–5 (1984)

As long as this transient inert coating remains, it:

1. restricts the subsequent adherence of plaque forming materials to the teeth, thus continuing the disruption of plaque formation;

2. continues to impart a "smooth" feeling to the mouth, and 3. prolongs the flavor perception of the dentifrice spray.

These features are described in Examples 1-6 below. The prolonged flavor perception, described as a "clean, just-brushed feeling," is particularly novel and unexpected.

The compositions of the present invention may also contain a fluorine-containing compound which has a beneficial effect on the care and hygiene of the oral cavity, such as sodium fluoride or stannous fluoride in an amount up to one percent, preferably between 0.1 percent by weight and one percent by weight of the dentifrice spray, based on the water soluble fluorine content thereof The compositions of the invention may also contain certain phosphate salts, such as sodium pyrophosphate, which have been shown to aid in the control of plaque and the calcified plaque called tartar.

The high flavor levels which can be pleasantly incorporated into this invention, whose frequent application is encouraged by the unique character of the invention, and which are retained in the mouth for surprisingly long time periods as discussed below in Examples 1–6 also contribute to the plaque controlling properties of this invention. For example, natural and synthetic flavor and sweetner agents as diverse as menthol, xylitol and glycyrrhizin are known to be beneficial towards plaque control and are included in the compositions of this invention (Reference: Segal, *J. Pharm. Sci.*, 74 pp. 79–81 (1985) and Makkinen, *J. Am. Dent. Assoc. III*, pp. 740–741).

In addition to the cleaning/coating compositions described above, preferred embodiments of the present invention use various viscosity control agents to impart certain viscosity characteristics to the products of the invention. It is believed that in these preferred embodiments of the invention, viscosity plays a role in achieving optimum mouth feel and flavor retention characteristics of the invention.

Viscosity between about 30 and about 600 cps is preferred and between about 70 and 250 cps is particularly preferred. Viscosity control agents are known in the prior art and can be selected from natural and synthetic gums such as gum tragacanth, methyl cellulose, polyvinyl pyrrolidone, and hydrophylic carboxyvinyl polymers such as those sold under the trademark Carbopol 934 Generally, about 0.1 percent to about 5 percent of a solution of viscosity control agent is used. See Table I.

Alcohol, flavors, colorants, sweetners, zylitol and humectants are also used to impart optimum cosmetic characteristics to the compositions of the present invention.

Generally, the flavoring component is present as a denaturant in the non-toxic alcohol component, i.e., ethyl alcohol. The conventional flavoring components are exemplified by the following materials, menthol, anise oil, benzaldehyde, bitter almond oil, camphor, cedar leaf oil, cinnamic aldehyde, cinnamon oil, citronella oil, clove oil, eucalyptol, heliotropine, lavendar oil, mustard oil, peppermint oil, phenyl salicylate, pine oil, pine needle oil, rosemark oil, sassafras oil, spearmint oil, thyme oil, thymol, wintergreen oil, lemon and orange oils, vanillin, and other flavoring oils generally regarded a safe (GRAS) by health authorities.

The compositions of the present invention generally contain about 30 to 65 percent, preferably about 40 to 50 percent by weight of water and from 30 to about 60 preferably about 40 to 55 percent by weight, most preferably about 45 percent by weight of a non-toxic alcohol such as ethanol. See Tables I and II. All percentages referenced in Tables I and II are percent by weight.

Additional adjuvants can be added to provide color, flavor, or sweetening effects, as desired. Examples of suitable sweetening agents include sorbitol, sodium cyclamate, saccharine, commercial materials such as Nutrasweet ® brand of aspartame and xylitol. The coloring agent is typically added in an amount of 0.01 percent to about 0.02 percent by weight. Citric acid is often utilized as a flavor additive. All types of flavoring materials are generally used in amounts of about 0.01 to about 5.0 percent by weight, preferably about 0.05 percent to about 3.0 percent by weight. (See Table I).

A buffering ingredient may also be added to the compositions of the invention in order to prevent natural degradation of the flavoring components. Generally, the pH of these compositions is adjusted to 3.5 to about 7, preferably from about 5 to about 6. The buffering ingredients such as an alkali metal salt of a weak organic acid, for instance, sodium benzoate, sodium citrate, sodium phosphate, or potassium tartrate is generally added in an amount of about 0.1 to about 1.0 percent by weight.

In addition to the water, alcohol, flavoring and pH buffering ingredients, the compositions of the invention can optionally contain at least one humectant selected from the group consisting of glycerine, xylitol, sorbitol and propylene glycol. Generally, such humectants are utilized in the proportion of about 3 percent to about 12 percent by weight based upon the total weight of the composition. Preferably, the humectant is utilized in an amount of about 3 to 4 percent by weight (See Table I).

EXAMPLES

The following examples provide a synopsis of dental and oral hygiene preparations combined according to the invention for application to wooden dental stimulators. The examples are intended for the purpose of illustration and are not to be construed as limiting in any way.

TABLE I

| | | | | (PERCENT BY WEIGHT) | | | | | | |
|---|---|---|---|---|---|---|---|---|---|---|
| Example | Cleaner(s) | Coating Substance | Thickener | Polyol(s) | Sweetener(s) | Flavor | Colorant | Water | Alcohol | Total % by Wt |
| 1 | Pluronic F-127 0.4 | Silicone A-F Emulsion (Dow Corning) 0.03 | Methocel K-4M 0.3 | Sorbital (70% Soln) 8.5 Glycerine 3.0 | Sodium Saccharin 0.65 | IFF Vanilla Mint #101 1.0 | FD&C Red #33 (17% Soln) 0.4 | 41.36 | 43.86 | 100 |
| 1a | same as 1 | none | same as 1 | same as 1 | same as 1 | same as 1 | same as 1 | 41.39 | 43.86 | 100 |
| 2 | same as 1 | Silicone A-F (Dow Corning) Emulsion 0.02 | same as 1 same as 1 | same as 1 same as 1 | same as 1 same as 1 | same as 1 same as 1 | same as 1 same as 1 | 41.37 | 43.86 | 100 |
| 3 | same as 1 | Silicone A-F (Dow Corning) | same as 1 same as 1 | same as 1 same as 1 | same as 1 same as 1 | same as 1 same as 1 | same as 1 same as 1 | 41.37 | 43.86 | 100 |

TABLE I-continued
(PERCENT BY WEIGHT)

| Example | Cleaner(s) | Coating Substance | Thickener | Polyol(s) | Sweetener(s) | Flavor | Colorant | Water | Alcohol | Total % by Wt |
|---|---|---|---|---|---|---|---|---|---|---|
| 4 | Sodium Lauryl Sulfate 1.5 | Emulsion 0.06 Silicone 190 NFF (Dow Corning) 2.5 | Methocel K-4M (29% Soln) 5.0 | Glycerine 10.0 | Sodium Saccharin 0.6 Honey 13.5 | Spearmint Oil 0.25 Peppermint Oil 0.25 | FD&C Red #33 (0.5% Soln) 2.0 | 9.95 | 54.45 | 100 |
| 5 | Sodium Lauroyl Sarcosinate 0.25 PEG 0.08 | Silicone A-F (Dow Corning) Emulsion 0.01 | Methocel K-4M 0.25 | Glycerine 3.5 | Sodium Saccharin 0.5 | IFF Citrus Mint #099 1.0 | None | 47.0 | 47.31 | 100 |
| 6 | Carbowax 4000 0.1 Tween 40 0.5 | Silicone A-F Emulsion (Dow Corning) 0.01 | Methocel K-4M 0.3 | Glycerine 3.0 Sorbitol (anhydrous) 6.0 | Sodium Saccharin 0.3 | IFF Spice Mint #098 0.5 | None | 44.0 | 45.29 | 100 |

Various combinations of cleaners and coating substances of the invention in a range of concentrations are set out in Table II below.

TABLE II

| Example | Cleaner | Concentration | Coating Substance | Conc. |
|---|---|---|---|---|
| 7 | sodium lauryl sulfate | 0.05 | Dow Corning Silicone AF emulsion | .005 |
| 8 | Pluronic 127 | 3.0 | Down Corning Silicone AF emulsion | .3 |
| 9 | sodium lauroyl sarcosinate | 0.1 | Down Corning Silicone AF emulsion | 0.01 |
| 10 | sodium lauryl sulfate | 1.5 | Dow Corning Silicon AF emulsion | 0.1 |
| 11 | Pluronic F-127 | 0.2 | Dow Corning Silicone AF emulsion | 0.02 |
| 12 | sodium lauroyl sarcosinate | 0.8 | Down Corning Silicone AF emulsion | 0.06 |
| 13 | sodium lauryl sulfate | 0.2 | Silicone glycol copolymer Dow Corning #190Nff | .5 |
| 14 | Pluronic F-127 | 0.3 | (same) | 5.0 |
| 15 | sodium lauryl sarcosinate | 0.4 | (same) | 1.5 |
| 16 | sodium lauryl sulfate | 0.5 | (same) | 3.0 |
| 17 | Pluronic F-127 | 0.6 | propylene glycol monostearate (Mazol PGMS) | 0.001 |
| 18 | sodium lauroyl sarcosinate | 0.7 | (same) | 0.5 |
| 19 | sodium lauryl sulfate | 0.8 | polyethylene glycol stearate (MAPEG S-40-K) | 0.01 |
| 20 | Pluronic F-127 | 0.9 | (same) | 0.2 |
| 21 | sodium lauryl sarcosinate | 1.0 | polyethylene (carbowax) | 0.05 |
| 22 | sodium lauryl sulfate | 1.1 | (same) | 0.1 |

While this invention has been described with reference to certain preferred embodiments, it will be recognized by those skilled in the art that many variations are possible without departing from the scope and spirit of the invention and it will be understood that it is intended to cover all changes and modifications of the invention disclosed herein for the purpose of illustration which do not constitute departures from the spirit and scope of the invention.

What is claimed is:

1. A porous dental stimulator impregnated with an ingestible, nonfoaming, oral hygiene cleaning preparation that coats mouth surfaces with a plaque matrix disrupting film, said cleaning preparation comprising:

a. a surfactant selected from the group consisting of:
  sodium lauryl sulfate,
  sodium lauroyl sarcosinate,
  polyethylene glycol stearate,
  polyethylene glycol monostearate,
  coconut monoglyceride sulfate,
  sodium alkyl sulfates,
  sodium alkyl sulfoacetates,
  block copolymers of polyoxyethylene/polyoxybutylene,
  allylpolyglycol ether carboxylates,
  polyethylene derivatives of sorbitan esters,
  propoxylated cetyl alcohol,
  block copolymers comprising a cogeneric mixture of conjugated polyoxybutylene polyoxylethylene compounds having as a hydrophobe a polyoxybutylene polymer of at least 1200 molecular weight,
  soap powder,
  and mixtures thereof, and b. a coating substance insoluble in said surfactant selected from the group consisting of:
  silicones,
  silicone glycol copolymers,
  polydimethyl siloxanes,
  long chain hydrocarbons,
  normal paraffins having a chain length of 16 carbon atoms or greater,
  paraffins with several loci of branching and unsaturation,
  carbowaxes,
  polymers with a limited solubility in ethanol and water solutions where the ethanol: water ratio is greater than 0.3:1 but have essentially no solubility in water or saliva at lower concentrations, and mixtures thereof, and c. wherein the cleaning preparation is present on said dental stimulator at a loading of from about 5 mg to about 50 mg per stimulator.

2. A treated dental stimulator comprising:

a. one or more segments of a wooden dental stimulator suitable for stimulating gums, said wood being selected from the group of woods consisting of balsa, birch and bass wood, said stimulator being loaded with a surfactant and coating substance cleaning preparation at a rate between about 5 mg and about 50 mg per segment of the wooden stimulator wherein:

b. the surfactant is selected from the group consisting of:
sodium lauryl sulfate,
sodium lauroyl sarcosinate,
polyethylene glycol stearate,
polyethylene glycol monostearate,
coconut monoglyceride sulfate, and mixtures thereof, and c. the coating substance, which is insoluble in said surfactant, is selected from the group consisting of:
silicone,
silicone glycol copolymer,
polydimethyl siloxanes,
normal paraffins having a chain length of about 16 carbon atoms
paraffins with several loci of branching and unsaturation,
carbowax,
and mixtures thereof.

3. A method of interrupting plaque matrix comprising periodically stimulating the gums, subgingival crevice, and interstitial spaces with a treated wooden dental stimulator, the treatment of which comprises the addition of an ingestible, nonfoaming, oral hygiene preparation that coats mouth surfaces with a plaque matrix disrupting film containing:

a. a surfactant selected from the group consisting of:
sodium lauryl sulfate,
sodium lauroyl sarcosinate,
polyethylene glycol stearate,
polyethylene glycol monostearate,
coconut monoglyceride sulfate,
sodium alkyl sulfates,
sodium alkyl sulfoacetates,
block copolymers of polyoxyethylene/polyoxybutylene,
allylpolyglycol ether carboxylates,
polyethylene derivatives of sorbitan esters,
propoxylated cetyl alcohol,
block copolymers comprising a cogeneric mixture of conjugated polyoxybutylene polyoxylethylene compounds having as a hydrophobe a polyoxybutylene polymer of at least 1200 molecular weight,
soap powder,
and mixtures thereof, and b. a coating substance insoluble in said surfactant selected from the group consisting of:
silicones,
silicone glycol copolymers,
polydimethyl siloxanes,
long chain hydrocarbons,
normal paraffins having a chain length of 16 carbon atoms or greater,
paraffins with several loci of branching and unsaturation,
carbowaxes,
polymers with a limited solubility in ethanol and water solutions where the ethanol: water ratio is greater than 0.3:1 but have essentially no solubility in water or saliva at lower concentrations,
and mixtures thereof.

4. The method of claim 3, wherein:

a. the surfactant is selected from the group consisting of:
sodium lauryl sulfate,
sodium lauroyl sarcosinate,
polyethylene glycol stearate,
polyethylene glycol monostearate,
coconut monoglyceride sulfate, and mixtures thereof, and b. the coating substance, which is insoluble in said surfactant, is selected from the group consisting of:
silicone,
silicone glycol copolymer,
polydimethyl siloxanes,
normal paraffins having a chain length of about 16 carbon atoms
paraffins with several loci of branching and unsaturation,
carbowax,
and mixtures thereof.

5. A method of treating gingivitis and other gum disease comprising: periodically massaging the gums with treated wooden dental stimulators, wherein the wooden stimulator:

a. is selected from the group consisting of bass wood, birch and balsa, b. is treated with an ingestible nonfoaming, oral hygiene preparation that coats mouth surfaces with a plaque matrix disrupting film comprising:

a. a surfactant selected from the group consisting of:
sodium lauryl sulfate,
sodium lauroyl sarcosinate,
polyethylene glycol stearate,
polyethylene glycol monostearate,
coconut monoglyceride sulfate,
sodium alkyl sulfates,
sodium alkyl sulfoacetates,
block copolymers of polyoxyethylene/polyoxybutylene,
allylpolyglycol ether carboxylates,
polyethylene derivatives of sorbitan esters,
propoxylated cetyl alcohol,
block copolymers comprising a cogeneric mixture of conjugated polyoxybutylene polyoxylethylene compounds having as a hydrophobe a polyoxybutylene polymer of at least 1200 molecular weight,
soap powder,
and mixtures thereof, and b. a coating substance insoluble in said surfactant selected from the group consisting of:
silicones,
silicone glycol copolymers,
polydimethyl siloxanes,
long chain hydrocarbons,
normal paraffins having a chain length of 16 carbon atoms or greater,
paraffins with several loci of branching and unsaturation, carbowaxes,
polymers with a limited solubility in ethanol and water solutions where the ethanol: water ratio is greater than 0.3:1 but have essentially no solubility in water or saliva at lower concentrations,
and mixtures thereof.
6. The method of claim 5, wherein:
a. the surfactant is selected from the group consisting of:
sodium lauryl sulfate,
sodium lauroyl sarcosinate,
polyethylene glycol stearate,
polyethylene glycol monostearate,
coconut monoglyceride sulfate,
and mixtures thereof, and
b. the coating substance, which is insoluble in said surfactant, is selected from the group consisting of:
silicone,
silicone glycol copolymer,
polydimethyl siloxanes,
normal paraffins having a chain length of about 16 carbon atoms
. paraffins with several loci of branching and unsaturation, carbowax,
and mixtures thereof.

* * * * *